US009193759B2

(12) United States Patent
Fachinger et al.

(10) Patent No.: US 9,193,759 B2
(45) Date of Patent: Nov. 24, 2015

(54) METHODS FOR THE RELEASE OF VIRUS-LIKE PARTICLES

(71) Applicant: Intervet Inc., Summit, NJ (US)

(72) Inventors: Vicky Fachinger, Bad Soden (DE); Melanie Sno, Venlo (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/176,249

(22) Filed: Feb. 10, 2014

(65) Prior Publication Data

US 2014/0234900 A1 Aug. 21, 2014

(30) Foreign Application Priority Data

Feb. 15, 2013 (EP) .................................... 13155370

(51) Int. Cl.
*C12P 21/06* (2006.01)
*C07K 1/14* (2006.01)
*C12P 21/00* (2006.01)
*C12N 7/00* (2006.01)
*A61K 39/00* (2006.01)

(52) U.S. Cl.
CPC ... *C07K 1/14* (2013.01); *C12N 7/00* (2013.01); *C12P 21/00* (2013.01); *A61K 39/00* (2013.01); *A61K 2039/5258* (2013.01); *C12N 2710/14043* (2013.01); *C12N 2750/10023* (2013.01); *C12N 2750/10051* (2013.01); *C12N 2750/14023* (2013.01); *C12N 2750/14051* (2013.01)

(58) Field of Classification Search
CPC ............ C07K 1/14; C12P 21/00; C12N 7/00; C12N 2710/14043; C12N 2750/10023; C12N 2750/14023; C12N 2750/10051; C12N 2750/14051; A61K 2039/5258; A61K 39/00
See application file for complete search history.

(56) References Cited

FOREIGN PATENT DOCUMENTS

WO 03/068993 A1 8/2003

OTHER PUBLICATIONS

Millan et al, Human Papillomavirus-Like Particles Vaccine Efficiently Produced in an Non-Fermentative System Based on Insect Larva, Protein Expression and Purification, Nov. 1, 2010, pp. 1-8, vol. 74, Elsevier, WO.
Fernandez-San Millan et. al., "Human papillomavirus-like particles vaccine efficiently produced in a non-fermentative system based on insect larva", Protein Expression and Purification, 2010, pp. 1-8, vol. 74.
Loudon et al., "Expression of the Outer Capsid Protein VP5 of Two Bluetongue Viruses, and Synthesis of Chimeric Double-Shelled Virus-like Particles Using Combinations of Recombinant Baculoviruses", Virology, 1991, pp. 793-801, vol. 182.
Schneemann et al., "Use of Recombinant Baculoviruses in Synthesis of Morphologically Distinct Viruslike Particles of Flock House Virus, a Nodavirus", Journal of Virology, 1993, pp. 2756-2763, vol. 67(5).
Smith et al., "A simplified Baculovirus-AAV Expression Vector System Coupled With One-step Affinity Purification Yields High-titer rAAV Stocks From Insect Cells", Molecular Therapy, 2009, pp. 1888-1896, vol. 17(11).
European Search Report for corresponding EP Application No. 13155370.3, dated May 15, 2013 (7 pages).

*Primary Examiner* — Reza Ghafoorian (57) ABSTRACT

The present invention relates to methods for the release of baculovirus-expressed Virus-like Particles (VLP's) of non-enveloped viruses from insect cells.

20 Claims, 8 Drawing Sheets

Insect cells without treatment

Insect cells with 0.3M NaCl in WFI

METHODS FOR THE RELEASE OF VIRUS-LIKE PARTICLES

The present invention relates to methods for the release of baculovirus-expressed Virus-like Particles (VLP's) of non-enveloped viruses from insect cells.

Nowadays, medical science heavily relies on vaccines when it comes to combating infectious diseases. Such vaccines may be live attenuated vaccines or inactivated vaccines, both with their own advantages and disadvantages. Live attenuated vaccines closely mimic the natural infection, and consequently they trigger an immune response that is comparable to the immune response triggered by the virulent form of a virus or microorganism. However, they may cause some unwanted side effects, and the level of attenuation is quite critical.

Inactivated vaccines on the other hand are safe, but they are in several cases not as efficacious as their live counterparts.

In the case of viral vaccines, a third type of vaccine is gaining more and more interest: the so-called Virus-like particle (VLP) based vaccine. Virus-like particles are particles that morphologically closely resemble the wild-type virus. They comprise all immunogenic components that are found on the wild-type virus, and they comprise these components in their natural organization and conformation. However they differ from the wild-type virus in that they are not capable of producing infectious progeny virus because they lack the viral genome.

As a consequence they are an attractive alternative for both live attenuated and inactivated virus vaccines.

VLP's are predominantly produced in vitro in cell systems. And in many cases they are produced in a baculovirus/insect cell expression system. These systems have the advantage that they are able to produce relatively large amounts of VLP's.

Proteins expressed in the Baculovirus expression vector system (BEVS) may be either secreted or non-secreted proteins. This implies that non-secreted VLPs have first to be released from the insect cells before they can be further purified. Standard methods for the release of VLP's comprise freeze-thawing, sonification, high shear mechanical methods, bead methods, "cell bomb", osmotic shock using a hypotonic medium, use of detergens and enzymatic methods.

However, all these methods unavoidably also result in cell disruption or lysis and release the whole content of the cell: RNA, DNA, proteins, cell organelles, cellular debris and in the case of baculovirus-based systems also live baculovirus into the surrounding medium. It is clear that most if not all of these components have to be removed before the VLP's are ready for use in a vaccine. The required level of purification implies an arduous multi-step process that includes many quality-checks.

Therefore, there is a clear need for methods for the release of non-secreted VLP's into the cell culture fluid that avoid releasing at the same time the cell's full nucleic acid and protein content.

It is an objective of the present invention to provide methods for the release of VLP's that reduce or even avoid the problems mentioned above.

The methods provided in the present invention are specifically suitable for the release of non-secreted VLP's of non-enveloped viruses expressed in baculovirus expression vector system using insect cells.

It was now surprisingly found that once insect cells comprising a non-enveloped VLP are mixed with a salt, such that the salt in water solution resulting from the mixing comprises at least 300 mOsmol/L of a salt of which the cation is selected from the group consisting of the alkali metals and the earth alkali metals, and of which the anion is selected from the group consisting of $Cl^-$, $Br^-$ or $I^-$, the cells release the VLP's without releasing their full cell content.

The method is especially suitable for insect cells when grown carrier-free in suspension.

Figure 4:
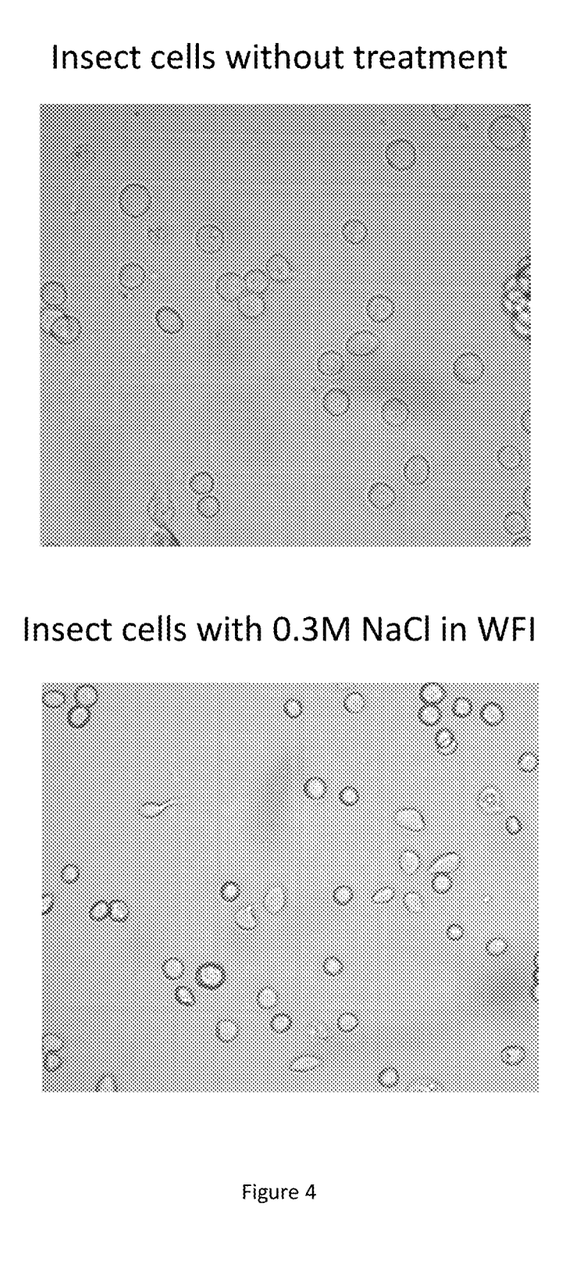
FIG. 4: This picture shows a comparison between insect cells in their culture medium (left picture) and insect cells after treatment with the method according to the invention (right picture).

This is indeed a highly surprising phenomenon: the method according to the present invention apparently leaves most of the cells intact, as can e.g. be seen in FIG. 4. The mechanism behind this release of VLP's is unclear.

Thus, a first embodiment of the present invention relates to methods for the release of baculovirus-expressed Virus-like Particles (VLP's) of non-enveloped viruses from insect cells, characterized in that the method comprises the step of mixing the insect cells with a salt, wherein the salt in water solution resulting from the mixing comprises at least 300 mOsmol/l of a salt of which the cation is selected from the group consisting of the alkali metals and the earth alkali metals, and of which the anion is selected from the group consisting of $Cl^-$, $Br^-$ and $I^-$.

For the purpose of this method, mixing the insect cells with a salt such that the salt in water solution resulting from the mixing comprises at least 300 mOsmol/l of a salt of which the cation is selected from the group consisting of the alkali metals and the earth alkali metals, and of which the anion is selected from the group consisting of $Cl^-$, $Br^-$ and $I^-$ is understood to comprise the following step: the cell culture fluid (the insect cells in their surrounding fluid) is mixed with a salt of which the cation is selected from the group consisting of the alkali metals and the earth alkali metals, and of which the anion is selected from the group consisting of $Cl^-$, $Br^-$ and to the extent that the resulting salt solution after mixing comprises at least 300 mOsmol/l of the salt.

It goes without saying that the mixing can be done in various ways; e.g. by adding salt in solid form to the cell culture fluid or by mixing a salt in water solution with the cell culture fluid.

The salt in water solution that is the result of the mixing, as described in the present invention, may e.g. comprise at least 150 mM NaCl/L (this gives the salt in water solution an osmolarity of at least 300 mOsmol of NaCl/L). If a salt solution as described in the present invention is made on the basis of $MgCl_2$, the salt in water solution resulting from the mixing would comprise at least 100 mM $MgCl_2$/L (this gives the salt in water solution an osmolarity of at least 300 mOsmol of $MgCl_2$/L).

The following examples serve as a mere illustration; if 100 ml of an insect cell culture comprising insect cells and culture medium is mixed with 100 ml of a 300 mM NaCl/L solution, the final 200 ml of fluid that results from this action comprises 150 mM NaCl/L. The final volume of the salt solution is of course of no relevance to the advantageous effects of the method according to the invention. If 75 ml of an insect cell culture comprising insect cells and culture medium is mixed with 25 ml of a 1200 mM NaCl/L solution, the final 100 ml of fluid that results from this action comprises 300 mM NaCl/L.

Figure 1:
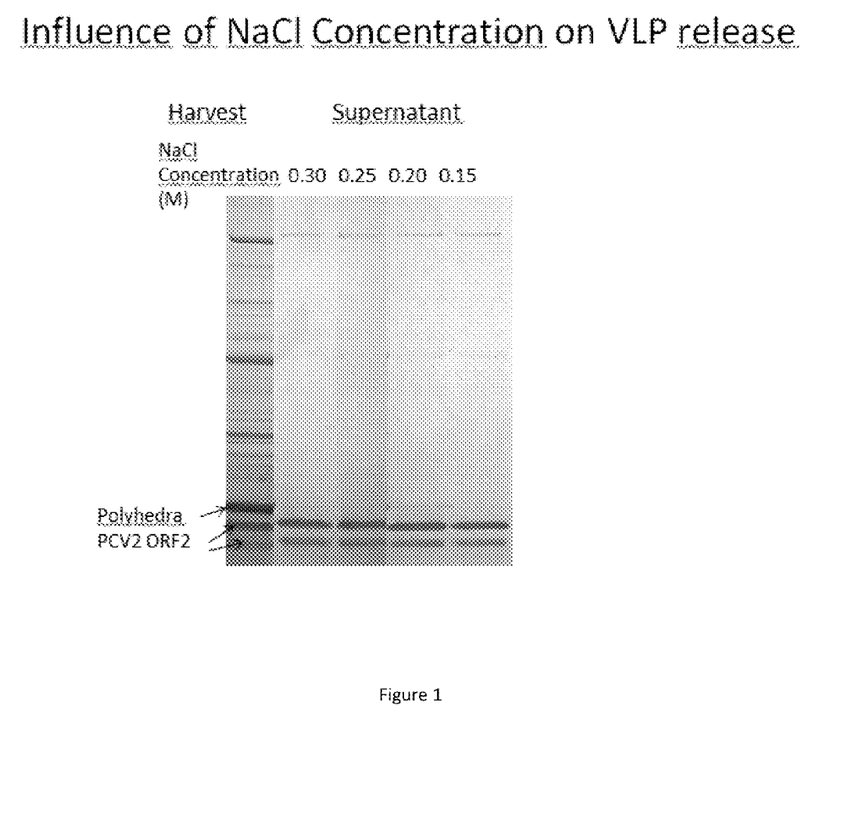
FIG. 1: This figure shows the effect of applying the method according to the invention using various concentrations of NaCl in water solution, at 40° C. to insect cells that comprise VLP's.

A visualization on gel of the unexpected phenomenon of the invention is given in FIG. 1. As can be seen from FIG. 1, the lanes showing the supernatant of the cells after treatment with the method according to the invention comprising the released VLP's are remarkably clean (see the Examples section for details).

Although, as the above, the final volume of the salt solution is not relevant for the method as such, in practice it is useful to introduce a concentration step before submitting the cell culture fluid to the mixing step according to the invention.

The main reason for a concentration step is that VLP-production for commercial purposes requires relatively large cell culture volumes.

It is not efficient to harvest VLP's directly from these large volumes; harvesting VLP's from a small volume requires much less handling.

The level of concentration in this step is not critical. Concentration of the cell culture fluid into a volume of half the amount of the original volume of the cell culture fluid (i.e. to 50% of the original volume) would already give a significant advantage in ease of harvesting. Further concentration to 40%, 30%, 25%, 20%, 15%, 10% or even 5% is preferred in that order of preference.

Concentration can be done in many ways, all known in the art. One frequently used method is ultrafiltration, e.g. in the form of tangential flow dialysis.

Another often used method is low-speed centrifugation. Low-speed centrifugation followed by removal of a part or all of the cell culture fluid leads to concentration and finally to the pelleting of the cells, but the cells would still be intact and still be surrounded by a small amount of culture fluid. Such cell pellets can then easily be mixed with a salt in water solution to give a salt in water solution as described in the invention.

For practical reasons, a very suitable method is to simply store the cell culture fluid comprising the cells and let gravitation pull the cells to the bottom of a vessel. After about 1-18 hours, depending on harvest volume and vessel size, by far most cells will be present in the bottom 10% of the cell culture fluid so that the cell-free upper 90% of the cell culture fluid can be discarded. This method avoids the task of centrifugation and/or ultrafiltration of large volumes of cell culture fluid. The VLP-containing cells in the bottom 10% of the cell culture fluid so obtained can then immediately be used in the step of mixing the insect cells with a salt as described in the invention.

Thus, a preferred form of this embodiment relates to a method according to the invention, characterized in that the step of mixing the insect cells with a salt is preceded by a concentration step in which the insect cells are concentrated.

In principle cations selected from the group consisting of the alkali metals and the earth alkali metals can be used for the method according to the invention. However, there's a preference for cations selected from the group consisting of $Na^+$, $Mg^{2+}$, $Ca^{2+}$ and $K^+$, because they are both inexpensive and acceptable for medicinal uses.

Therefore, another preferred form of this embodiment of the present invention relates to a method according to the invention, characterized in that the cation is selected from the group consisting of $Na^+$, $Mg^{2+}$, $Ca^{2+}$ and $K^+$.

A preferred anion is $Cl^-$, because salts having a $Cl^-$ anion are inexpensive and they are highly acceptable for medicinal uses.

Thus, a more preferred form of this embodiment relates to a method according to the invention, characterized in that the salt is selected from the group consisting of $NaCl$, $KCl$, $CaCl_2$ and $MgCl_2$.

The cell culture fluid comprising the insect cells that carry the VLP's, additionally comprises many components that are necessary for culturing the cells. It also comprises waist products of the cells.

These products are unwanted side products that may be detrimental to the final vaccine comprising the VLP's.

Such components are thus preferably separated from the insect cells comprising the VLP's before applying the method according to the invention to the cells. This can easily be done by pelleting the cells, discarding the supernatant and resuspending the cells in a salt solution as described in the invention. If this is done carefully, by far most of the supernatant can be removed. In that case, the salt in water solution resulting from the mixing of the cells and the salt essentially consists of a salt as described in the invention, and water. Essentially here means that the salt in water solution resulting from the mixing comprises less than 10% cell culture fluid. Preferably, the water solution resulting from the mixing comprises less than 8%, less than 6%, less than 4% or even less than 2% cell culture fluid.

Thus, a preferred form of this embodiment relates to methods according to the invention, characterized in that the salt in water solution resulting from the mixing essentially consists of a salt as described in the invention, and water.

The method according to the present invention is suitable for non-secreted non-enveloped VLP's which are expressed in BEVS in general.

The method is thus i.a. suitable for BEVS-derived VLP's of members of the family Parvoviridae and Circoviridae; virus families that have several members for which currently VLP's are made on a commercial basis.

Therefore, another preferred form of this embodiment of the present invention relates to a method according to the invention, characterized in that the non-enveloped virus is a member of the family Parvoviridae or Circoviridae.

Examples of important Parvoviridae and Circoviridae vaccines for use in veterinary medicine on the basis of non-enveloped virus that can successfully be administered in the form of VPL's made in a baculovirus-based insect cell system are Porcine Parvovirus (PPV) and Porcine Circovirus type 2 (PCV2).

Therefore, a more preferred form of this embodiment of the present invention relates to a method according to the invention, characterized in that the non-enveloped virus is a Porcine Parvovirus (PPV) or a Porcine Circovirus type 2 (PCV2).

The production of VLP's in BEVS in principle also leads to the production of baculoviruses. Such baculoviruses are an unwanted side product of the VLP's and therefore, they have to be removed or at least inactivated.

It was now even more surprisingly found that if the salt in water solution is kept at a temperature of between 30-55° C., preferably between 35-50° C., more preferably between 40-45° C., the amount of live baculovirus decreases significantly. On top of that, the amount of antigen released also increases significantly when the temperature is increased.

This decrease is very advantageous, because the amount of virus to be inactivated after applying the method according to the invention is relatively low, and therefore lower amounts of inactivating chemicals have to be used.

Merely as an example; when the salt in water solution is kept at a temperature of between 30-40° C., a decrease in virus titer of between 1000 to 10.000 times can easily be obtained. The time during which a certain temperature must be applied depends on the temperature as selected: at a temperature of around 40° C., a 10 times decrease in virus titer is obtained after 1 hour, whereas at a temperature of around 35° C., such a decrease is obtained after 5-6 hours. In general, keeping the salt in water solution resulting from the mixing at a certain temperature for 18-24 hours is suitable anyway.

Two specimens of insect cells that are very commonly used for VLP-expression are SF9 or SF21 cells. The method described in the present invention can very successfully be applied to both these cells.

Thus, another preferred form of this embodiment of the present invention relates to a method according to the invention wherein the insect cells are SF9 or SF21 cells.

The described method is usually a part of generally applied methods for the purification of baculovirus-expressed Virus-like Particles (VLP's) of non-enveloped viruses, that comprise a number of steps amongst which are the steps of a) infecting insect cells with a recombinant baculovirus encoding VLP-proteins, b) culturing the insect cells, c) releasing the VLP's from the insect cells and d) isolating the VLP's.

It is step c), the step of releasing the VLP's that would highly benefit from the method according to the invention.

Thus, again another embodiment of the present invention relates to methods for the purification of baculovirus-expressed Virus-like Particles (VLP's) of non-enveloped viruses, wherein the method comprises the steps of:
 a) infecting insect cells with a recombinant baculovirus encoding VLP-proteins
 b) culturing the insect cells
 c) releasing the VLP's from the insect cells
 d) isolating the VLP's
characterized in that step c comprises the method according to the present invention for the release of the VLP's.

EXAMPLES

Example 1

Production of PCV2 VLP's

In this Example, BEVS-derived PCV2 VLP's was used. The construction of this recombinant baculovirus was described earlier in detail in US-Patent US 2001/0064765. The virus is further referred to as BacPCV-2-ORF-2 virus.

In order to obtain maximum amounts of expression product, pilot experiments were carried out to optimize the conditions for obtaining recombinant PCV-2 ORF-2 VLP's. All experiments were carried out using *Spodoptera frugiperda* 21 (Sf21) cells in suspension culture at 28° C. BacPCV-2-ORF-2 virus at the $4^{th}$ passage level from the Master seed was used for infection. For optimized production, cell density at the time of infection was $1.4 \times 10^6$ cells/ml, the multiplicity of infection (MOI) was 0.01 and culture was continued for 6 days following infection. The resulting mixture was named expression product harvest. Samples of cell culture fluid before and after low-speed centrifugation were subjected to denaturing SDS-polyacrylamide gel-electrophoresis according to the method of Laemmli (Laemmli, U. K. (1970). *Nature* 227, 680-685). The 4-12% gradient gels used were stained with Coomassie Brilliant Blue. All gels in the Examples are also denaturing SDS-polyacrylamide gels according to Laemmli.

Example 2

Release of VLP's from Insect Cells

Cells were harvested according to Example 1. In FIG. 1, the lane with heading "harvest" shows the protein content of cell culture harvest. This lane shows all proteins present in the culture fluid and the cells, including cellular proteins, baculovirus proteins and VLP-related proteins.

Following centrifugation of the harvest at 200 g, 90% of the cell free supernatant was exchanged by an equal volume of a salt in water solution, such that the final concentration after mixing was 0.15, 0.20, 0.25 and 0.30 mM NaCl. These mixtures were kept for 18 hours at 40° C. and the remaining cells were subsequently spun down through centrifugation at 3000 g. The supernatants were subjected to gel electrophoresis.

As can be seen in FIG. 1, in the lanes under the heading "Supernatant", the supernatant comprises practically pure PCV2 VLP protein (and trace amounts of non-VLP proteins).

Example 3

Comparison of Alkali Salts and Phosphate Buffers

In this experiment, cell culture fluid was harvested, cells were pelleted at 200 g, 90% of the supernatant was removed and cells were resuspended in an equal volume of either PB (250 mM phosphate buffer, pH 7.4, PB+0.5 M NaCl, H2O (=WFI=water-for-injection) and a 0.5 M NaCl in water solution as described in the invention.

Figure 2:
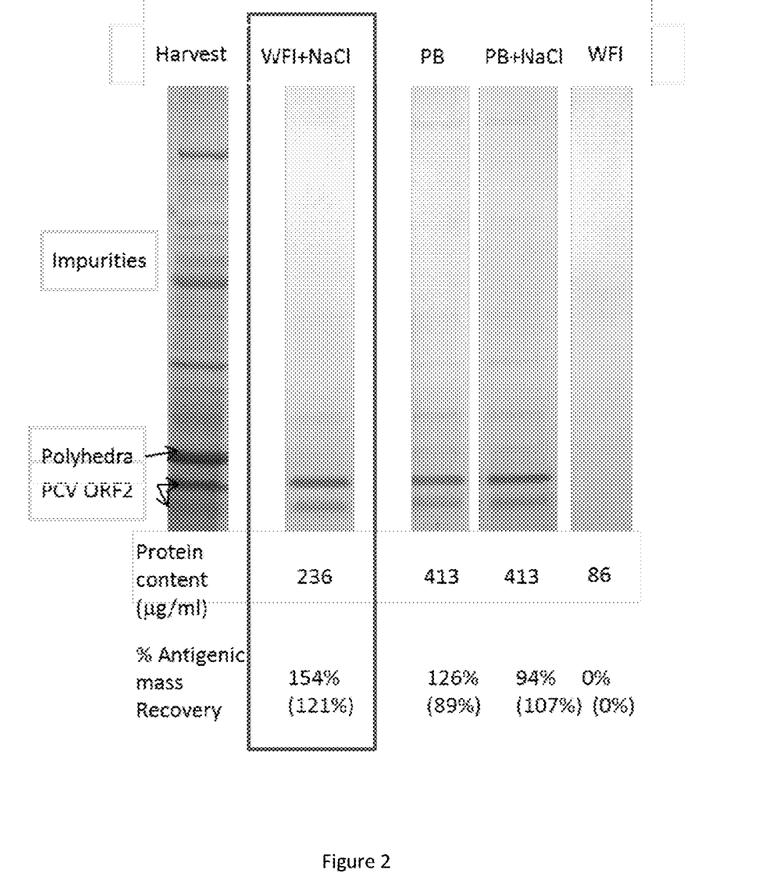
FIG. 2: This figure shows the effect of applying the method according to the invention using various salts in a salt in water solution, to insect cells that comprise VLP's.

Incubation was done at 40° C., overnight. Cells were subsequently removed by centrifugation at 3000 g. It can be seen from FIG. 2 that WFI alone does not release the VLP's, whereas PB+NaCl, NaCl in water solution and PB do release VLP's. As follows from the lane WFI+NaCl (=water-for-injection+NaCl, =NaCl in water solution), this gives the highest amount of pure VLP's, and the lowest background of non-VLP-related proteins.

The antigenic mass (expressed in Antigenic Units per ml-AU/ml) of all samples was determined by ELISA relative to a reference standard of known antigenic mass. Subsequently, the recovery rates (in %) of all test samples were calculated relative to that of the harvest sample. As an alternative method the intensity of the PCV2 specific protein bands on the gel were calculated relative to the intensity of the PCV2 specific protein band of the harvest sample.

Example 4

Comparison of Alkali Salts and Phosphate Buffers at Elevated Temperatures

In this example, cell culture fluid was harvested, cells were pelleted at 200 g, 90% of the supernatant was removed and cells were resuspended in an equal volume of either PB (250 mM phosphate, pH 7.4, PB+0.5 M NaCl, 0.01 M PBS (8 g NaCl/L, 0.2 g KCl/L, 1.44 g $Na_2HPO_4$/L, 0.2 g $KH_2PO_4$/L, pH 7.1) and a 0.5 M NaCl in water solution as described in the invention.

Several dilutions were made, in order to compare the effect of the level of dilution of the cell culture fluid. In one experiment the cells in 30 ml of the harvested cell culture fluid were concentrated 10 times and subsequently mixed with salt in water solution to an end volume of 50 ml. In a second experiment the cells in 30 ml of the harvested cell culture fluid were concentrated 10 times and subsequently mixed with salt in water solution to an end volume of 25 ml. In a third experiment, the cells in 30 ml of the harvested cell culture fluid were concentrated 10 times and subsequently mixed with salt in water solution to an end volume of 10 ml.

Incubation was done at 40° C., overnight. Cells were subsequently removed by centrifugation at 3000 g. It can be seen from the gel in FIG. 3, that PB, PB+NaCl, PBS and NaCl in water solution (WFI+NaCl) all do release VLP's. As follows from the lane WFI+NaCl (=water-for-injection+NaCl, =NaCl in water solution), this gives the highest amount of pure VLP's, and the lowest background of non-VLP-related proteins. The same effect is seen for all three concentrations.

Figure 3:
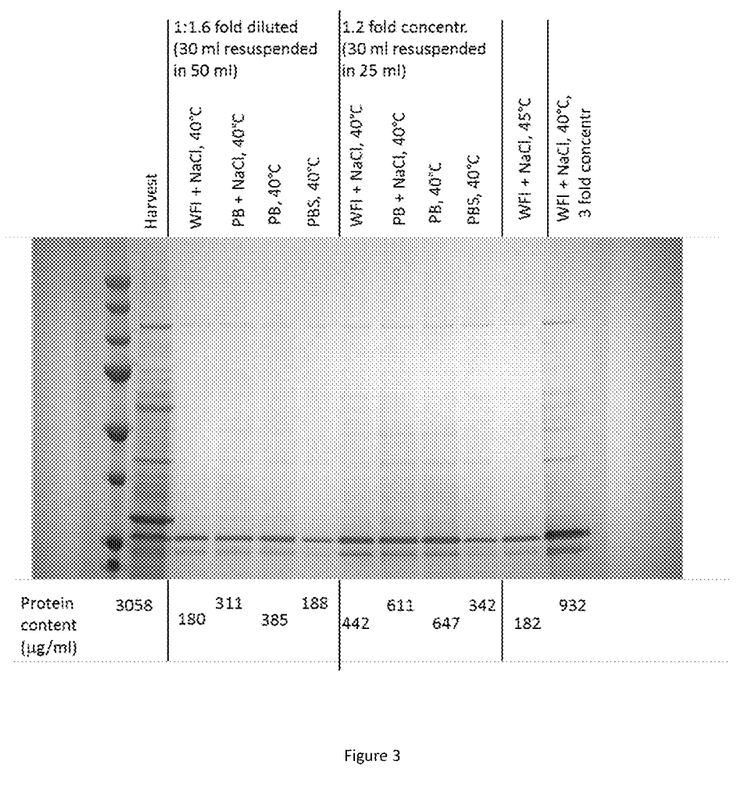
FIG. 3: This figure shows the effect of applying the method according to the invention using various salts in a salt in water solution at an elevated temperature, to insect cells that comprise VLP's.

In addition, the experiment with WFI+NaCl was also done at 45° C. As can be seen from lane "WFI+NaCl, 45° C.", incubation at this temperature gives a picture comparable to WFI+NaCl treatment at 40° C.: VLP-protein with a comparable low amount of protein impurities.

Example 5

Behavior of Cells in the Salt in Water Environment

In this experiment, microscopic pictures were made of insect cells in cell culture fluid and cells that were treated according to a method according to the invention. Cells were either kept as untreated cell culture fluid or were subjected to a method according to the invention, in this case the mixing with a salt in water solution such that the salt in water solution resulting from the mixing comprised 0.3 M NaCl/L.

FIG. 4 shows the results: the left picture shows the insect cells without treatment, whereas the right picture shows the insect cells in salt in water solution comprising 0.3 M NaCl/L after mixing. As can immediately be seen, the cells in the right picture are indeed still intact, and they are even slightly smaller in size compared to the cells in the left picture, due to their presence in the hyperosmotic environment of the salt in water solution comprising 0.3 mM NaCl/L.

Example 6

Influence of Incubation Temperature on Baculovirus Titer

In this Example, 30 ml of cells was harvested by low-speed centrifugation, 90% of the cell-free culture fluid was removed and the remaining cell pellet was subsequently resuspended in 25 ml salt in water solution to an end concentration of 0.5 M NaCl/L.

Figure 5:
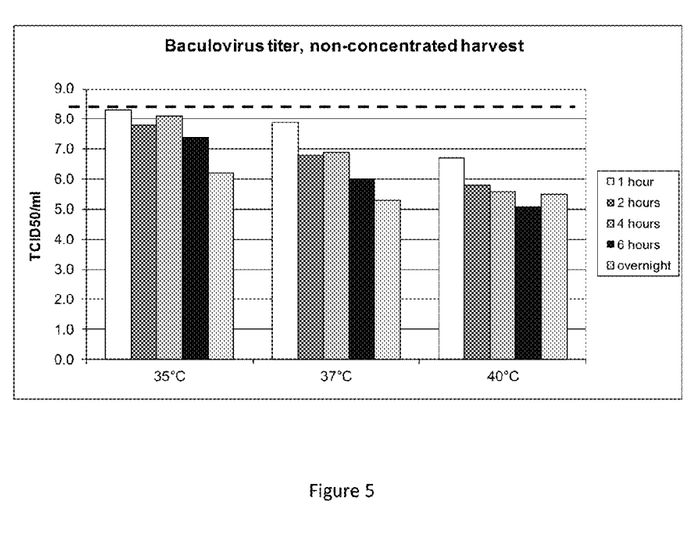
FIG. 5: This picture shows the influence of prolonged incubation at elevated temperature on baculovirus titer.

The suspension thus obtained was subjected for 1, 2, 4, 6 or 18 hours (overnight) to temperatures of 35° C., 37° C., and 40° C. Cells were subsequently removed by centrifugation at 3000 g. As can be seen from FIG. 5, a decrease of baculovirus titer of about 100 times can be obtained overnight at 35° C. At 40° C., a decrease of 100 times is already obtained after 1-2 hours, whereas a decrease of 1000 times is obtained after 6-18 hours.

Example 7

Comparison of Various Concentrations of Several Alkali Metals

This experiment compares the VLP-release by different salts. Cells were harvested as described above, 90% of cell free cell culture fluid volume was removed. Thereafter, various salt in water solutions were added whereby the volume of the salt in water solutions was always equal to that of the concentrated harvest volume in order to achieve an end concentration of the cells of 5 fold. The test was performed with various concentrations of NaCl, KCl, MgCl$_2$ and CaCl$_2$. Cells were subsequently removed by centrifugation at 3000 g.

The concentration after mixing is presented in table 1 below.

TABLE 1

|   |   | Recovery Rate Gel | AM (AU/ml) |
|---|---|---|---|
| 2 | A074, Harvest day 7 | 100 | 25183 |
| 3 | 0.3M NaCl (5x conc.)* | 204 | 111364 |

TABLE 1-continued

|   |   | Recovery Rate Gel | AM (AU/ml) |
|---|---|---|---|
| 4 | 150 mM NaCl | 182 | 76266 |
| 5 | 300 mM NaCl | 191 | 80806 |
| 6 | 100 mM MgCl2 | 198 | 83782 |
| 7 | 200 mM MgCl2 | 191 | 59528 |
| 8 | 100 mM CaCl2 | 157 | 60327 |
| 9 | 200 mM CaCl2 | 75 | 60659 |
| 10 | 150 mM KCl | 162 | 61900 |
| 11 | 300 mM KCl | 179 | 86528 |

Figure 6:
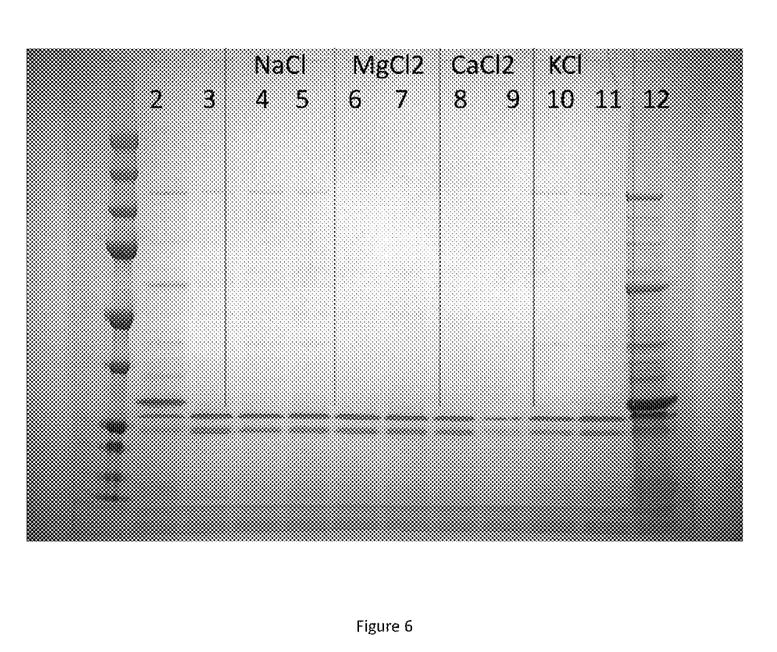
FIG. 6: This figure shows the effect of applying the method according to the invention using NaCl, $MgCl_2$, $CaCl_2$ and KCl as the alkali salt in a salt in water solution, to insect cells that comprise VLP's.

*this sample is derived from the same harvest but was treated with 0.3M NaCl on a different day than the rest of the samples The results are presented in FIG. 6. Lane 2 shows the proteins as present in the harvest (following a fivefold dilution of the samples (exception: Lane 12: undiluted harvest sample).

The recovery rate of the harvest sample on gel (table 1) is indicated in the table as 100, the relative recovery as determined on gel is presented in the second-right column of table 1. The antigenic mass recovery is presented in the right column of table 1. It follows from both the gel in FIG. 6 and the table that all treatments have a higher recovery rate than the preparation in lane 2 (harvest), and all treatments provide clean VLP preparations. (The relatively low recovery rate value in lane 9 is considered to be an artifact, since the Antigenic mass determination of the preparation as tested in lane 9 shows a high recovery rate as expected).

Figure 7:
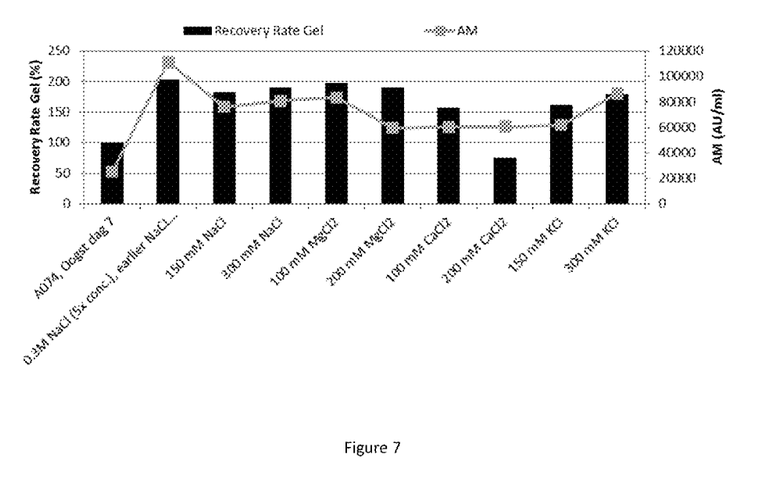
FIG. 7: This figure shows the relation between the amount of VLP's obtained using the method according to the invention as determined on gel and as determined by antigenic mass ELISA.

FIG. 7 shows that there is a good correlation between the recovery rate of VLP's as determined on gel and the recovery rate of VLP's as determined by antigenic mass determination on the basis of a standard ELISA test.

Example 8

Applying the Method to SF9 and SF21 Cells Producing Porcine Parvovirus

This experiment aimed at showing that the method is equally suitable for other non-enveloped non-secreted VLP's. In this experiment, a BEVS-derived VLP of the Parvoviridae is chosen: Porcine Parvovirus PPV). Also, in this experiment two different species of commonly used insect cells were used: SF9 cells and SF21 cells.

SF9 and SF21 cells were infected with a recombinant baculovirus expressing Porcine Parvovirus VLP's. ("harvest", FIG. 8, Lanes 2 and 7). Thereafter cells were pelleted at 200 g, 90% of the supernatant was removed (FIG. 8, Lanes 4 and 9) and cells were resuspended either in an equal volume of PBS (FIG. 8, lanes 3 and 8) or 0.3 M NaCl in water solution.

Figure 8:
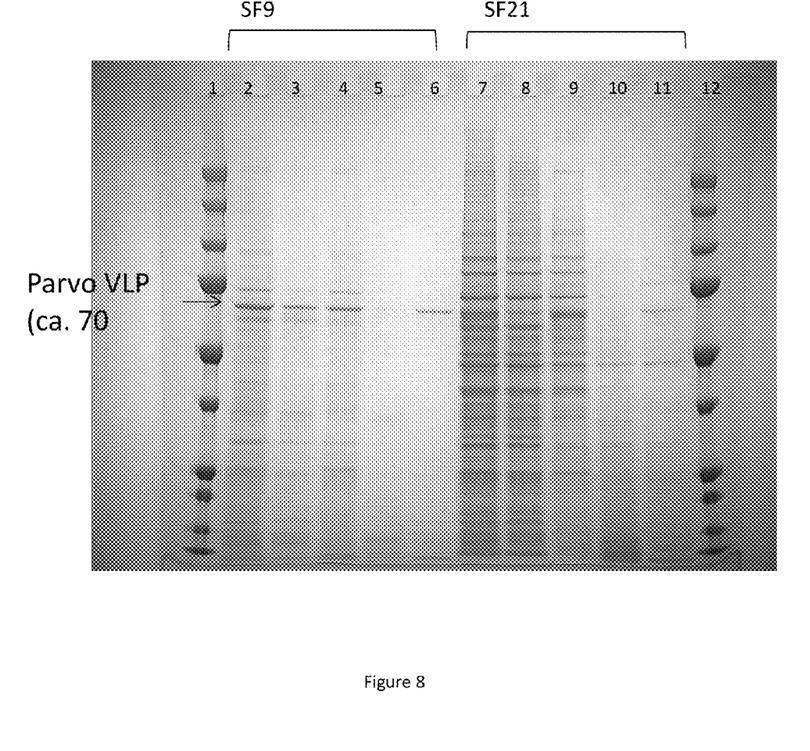
FIG. 8: This figure shows the effect of applying the method according to the invention to two different insect cell lines that express Baculovirus-derived Porcine Parvovirus VLP's. Lane 2, 7: harvest. Lane 3, 8: harvest, pellet resuspended in PBS. Lane 4, 9: harvest supernatant. Lane 5, 10: harvest, 0.3 M NaCl O/N 40° C., pellet. Lane 6, 11: harvest, 0.3 M NaCl 0/N 40° C., supernatant.

Following incubation of the NaCl treated samples overnight at 40° C., samples were centrifugated at 3000 g, the supernatant was collected (FIG. 8, lanes 6 and 11) and the pellet was resuspended in an equal volume of PBS (FIG. 8, lanes 5 and 10).

FIG. 8 shows the results of the method, when applied to PPV-VLP's produced in SF9 and SF21 cells. Lane 2: harvest; lane 3: harvest, pellet resuspended in PBS, lane 4: harvest supernatant; lane 5: harvest, 0.3 M NaCl overnight 40° C., pellet; lane 6: harvest, 0.3 M NaCl overnight 40° C., supernatant; lane 7: harvest; lane 8 harvest, pellet resuspended in PBS, lane 9: harvest supernatant; lane 10: harvest, 0.3 M NaCl overnight 40° C., pellet; lane 11: harvest, 0.3 M NaCl overnight 40° C., supernatant.

As follows from lane 5 when compared to lane 3, the treatment according to the method of the present invention releases practically all VLP's from the insect cells: the cells pelleted after the treatment, as shown in lane 5 comprise hardly or no VLP's. From lane 4 when compared to lane 3 it can be seen that contrary to what is seen with PCV2 VLP's, the insect cells producing CPV VLP's already release a part of the VLP's in the supernatant. The reason for this is unknown. Nevertheless, the method according to the invention can very suitably be applied to these CPV VLP's too, because without applying the method of the present invention, a very considerable amount of the CPV VLP's remains trapped in the cells after harvest.

The invention claimed is:

1. A method for the release of baculovirus-expressed Virus-like Particles (VLP's) of non-enveloped viruses from insect cells, wherein the method comprises the step of mixing the insect cells with a salt, wherein the salt in water solution resulting from the mixing comprises at least 300 mOsmol/l of a salt of which the cation is selected from the group consisting of the alkali metals and the earth alkali metals, and of which the anion is selected from the group consisting of $Cl^-$, $Br^-$, and $I^-$; wherein the non-enveloped virus is a member of the family Circoviridae.

2. The method of claim 1, wherein the step of mixing the insect cells with a salt is preceded by a concentration step during which the insect cells are concentrated.

3. The method of claim 1, wherein the cation is selected from the group consisting of $Na^+$, $Mg^{2+}$, $Ca^{2+}$, and $K^+$.

4. The method of claim 3, wherein the salt is selected from the group consisting of NaCl, KCl, $CaCl_2$, and $MgCl_2$.

5. A method for the release of baculovirus-expressed Virus-like Particles (VLP's) of non-enveloped viruses from insect cells, wherein the method comprises the step of mixing the insect cells with a salt, wherein the salt in water solution resulting from the mixing comprises at least 300 mOsmol/l of a salt of which the cation is selected from the group consisting of the alkali metals and the earth alkali metals, and of which the anion is selected from the group consisting of $Cl^-$, $Br^-$, and $I^-$; wherein the non-enveloped virus is a member of the family Parvoviridae.

6. The method of claim 1, wherein the salt in water solution is kept at a temperature of between 35-50° C.

7. The method of claim 6, wherein the salt in water solution is kept at a temperature of between 40-45° C.

8. The method of claim 6, wherein the insect cells are SF9 or SF21 cells.

9. A process for purifying baculovirus-expressed Virus-like Particles (VLP's) of non-enveloped viruses, said process comprising the steps of:
   a) infecting insect cells with a recombinant baculovirus encoding VLP-proteins;
   b) culturing the insect cells;
   c) releasing the VLP's from the insect cells by the method of claim 1; and
   d) isolating the VLP's.

10. A process for purifying baculovirus-expressed Virus-like Particles (VLP's) of non-enveloped viruses, said process comprising the steps of:
   a) infecting insect cells with a recombinant baculovirus encoding VLP-proteins;
   b) culturing the insect cells;
   c) releasing the VLP's from the insect cells by the method of claim 5; and
   d) isolating the VLP's.

11. The method of claim 5, wherein the step of mixing the insect cells with a salt is preceded by a concentration step during which the insect cells are concentrated.

12. The method of claim 5, wherein the cation is selected from the group consisting of $Na^+$, $Mg^{2+}$, $Ca^{2+}$, and $K^+$.

13. The method of claim 12, wherein the salt is selected from the group consisting of NaCl, KCl, $CaCl_2$, and $MgCl_2$.

14. The method of claim 5, wherein the salt in water solution is kept at a temperature of between 35-50° C.

15. The method of claim 14, wherein the salt in water solution is kept at a temperature of between 40-45° C.

16. The method of claim 14, wherein the insect cells are SF9 or SF21 cells.

17. A method for the release of baculovirus-expressed Virus-like Particles (VLP's) of non-enveloped viruses from insect cells, wherein the method comprises the step of mixing the insect cells with a salt, wherein the salt in water solution resulting from the mixing comprises at least 300 mOsmol/l of a salt of which the cation is selected from the group consisting of the alkali metals and the earth alkali metals, and of which the anion is selected from the group consisting of $Cl^-$, $Br^-$, and $I^-$; wherein the salt in water solution is kept at a temperature of between 35-50° C.

18. The method of claim 17, wherein the step of mixing the insect cells with a salt is preceded by a concentration step during which the insect cells are concentrated.

19. The method of claim 17, wherein the salt in water solution is kept at a temperature of between 40-45° C.

20. The method of claim 19, wherein the insect cells are SF9 or SF21 cells.

* * * * *